US006544957B2

(12) United States Patent
Kern et al.

(10) Patent No.: US 6,544,957 B2
(45) Date of Patent: Apr. 8, 2003

(54) METHODS AND REAGENTS FOR FACILITATING TRANSCRIPTION

(75) Inventors: Scott E. Kern, Hunt Valley, MD (US); Gloria Su, Cockeysville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/752,673

(22) Filed: Jan. 3, 2001

(65) Prior Publication Data

US 2001/0031722 A1 Oct. 18, 2001

Related U.S. Application Data

(60) Provisional application No. 60/174,500, filed on Jan. 4, 2000.

(51) Int. Cl.[7] .............................................. A61K 48/00
(52) U.S. Cl. ..................... 514/44; 435/91.4; 435/320.1; 435/455; 424/93.2; 514/2
(58) Field of Search ................................ 514/23, 2, 44; 435/320.1, 325, 455, 91.4, 458; 424/93.2

(56) References Cited

U.S. PATENT DOCUMENTS

| 4,690,918 A | 9/1987 | Beppu |
| 5,834,249 A | 11/1998 | Furukawa |
| 5,993,845 A | 11/1999 | Geerts |

OTHER PUBLICATIONS

Verma et al. Gene therapy promises, problems and prospects pp. 239–242 vol. 389 1997.*
Anderson Human gene therapy pp. 25–30 vol. 392 1998.*
Gloria H. Su, et al., "A Novel Histone Deacetylase Inhibitor Indentified by High–Throughput Transcriptional Screen of a Compound Library", Cancer Research 60, 3137–3142, Jun. 15, 2000.

* cited by examiner

Primary Examiner—Dave T. Nguyen
(74) Attorney, Agent, or Firm—Banner & Witcoff, Ltd.

(57) ABSTRACT

A previously unknown histone acetylase inhibitor, 6-(1,3-Dioxo-1H, 3H-benzo[de]isoquinolin-2-yl)-hexanoic acid hydroxyamide, termed "scriptaid," can be used to enhance transcription. Scriptaid can be added to transactivation assays, or can be used, for example, to increase production of therapeutic polypeptides in vitro and in vivo.

31 Claims, 7 Drawing Sheets

FIG. 2
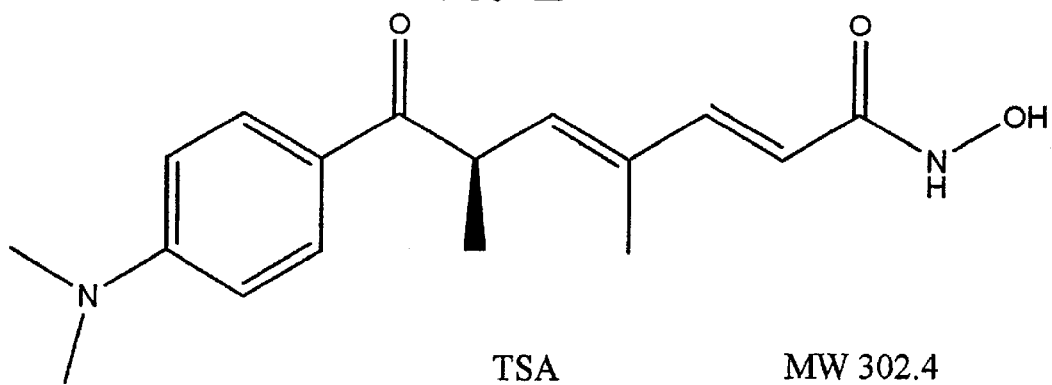
TSA         MW 302.4
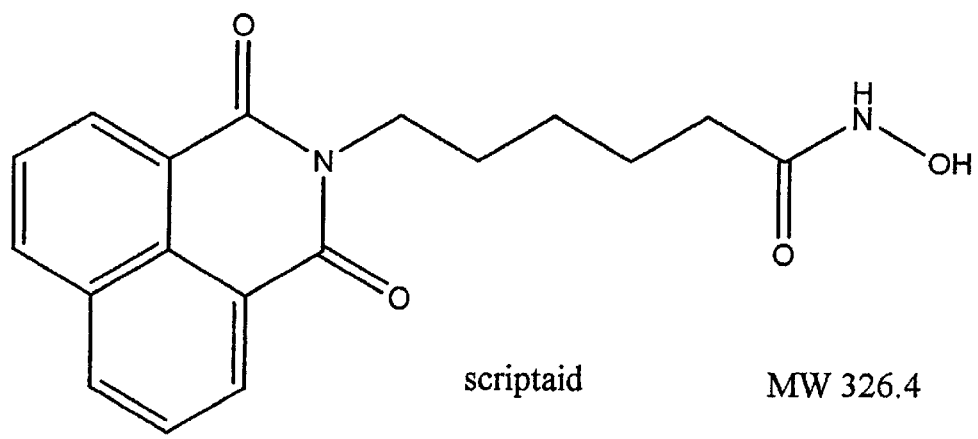
scriptaid   MW 326.4
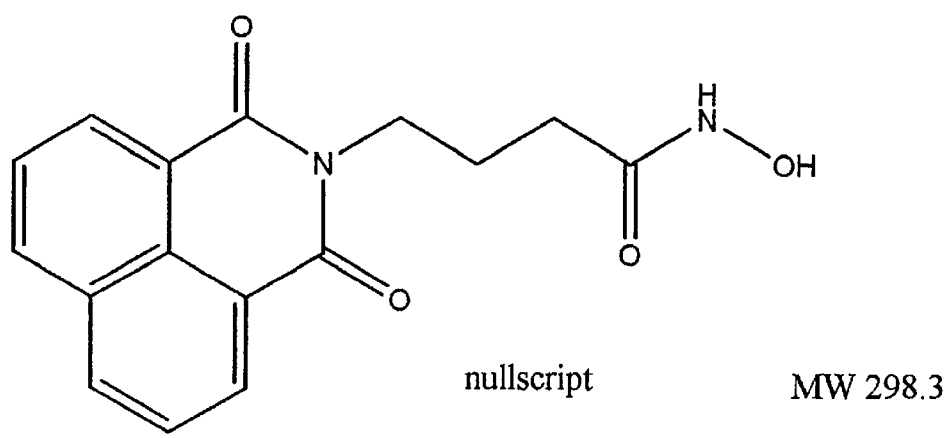
nullscript  MW 298.3

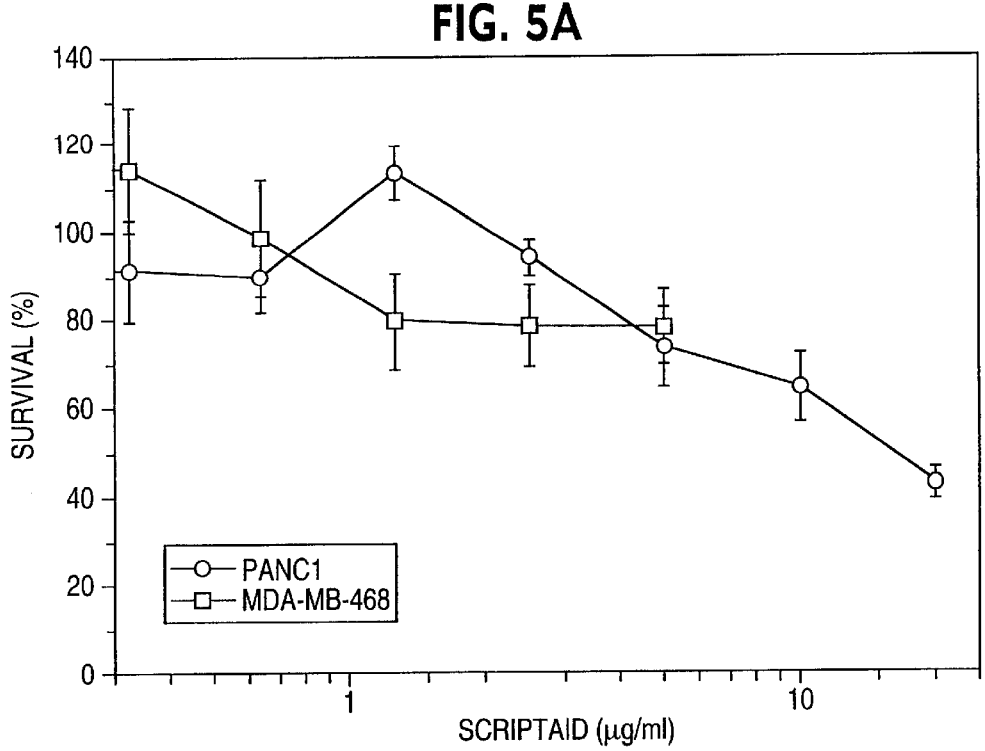
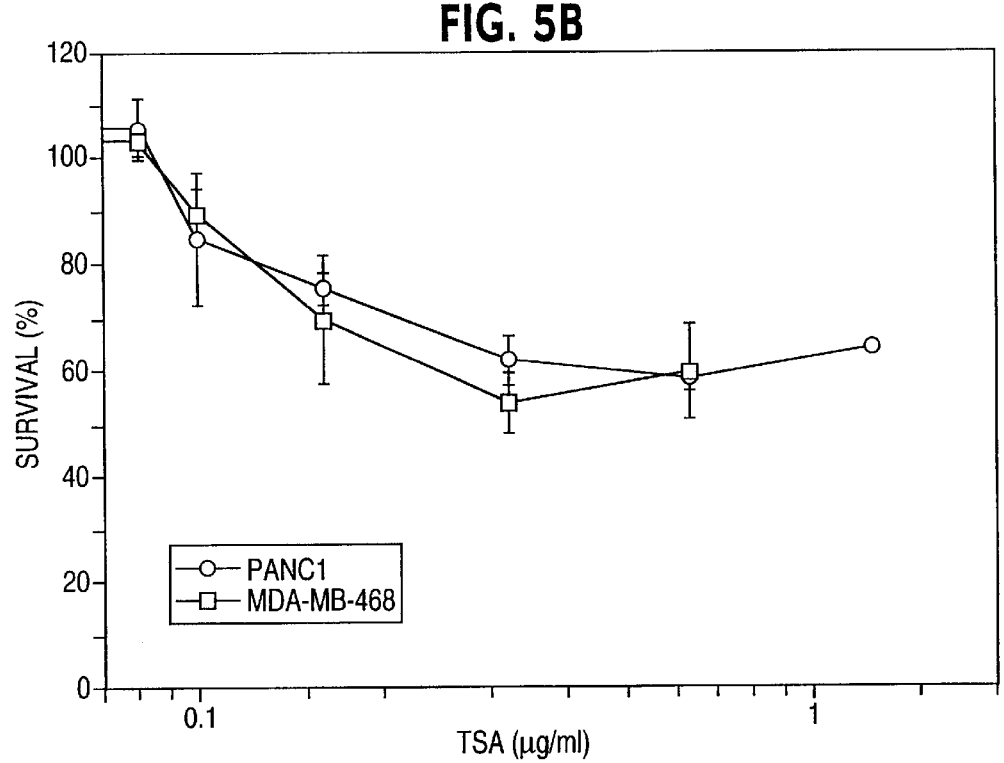

US 6,544,957 B2

METHODS AND REAGENTS FOR FACILITATING TRANSCRIPTION

This application claims the benefit of Ser. No. 60/174,500 filed Jan. 4, 2000, which is incorporated herein by reference.

The work described herein was supported by National Institutes of Health grants CA 62924 and CA68228. The government therefore has certain rights in the invention.

TECHNICAL FIELD OF THE INVENTION

The invention relates to the use of a newly identified histone deacetylase inhibitor to facilitate transcription.

BACKGROUND OF THE INVENTION

The strength of background transcriptional repression, which acts on general-utility promoters, is currently under-appreciated. In some reporter systems, negative effects on transcription (repression) may completely overshadow the positive effects. In other cases, for example, a two-fold induction seen in an experimental situation may not always represent a 100% increase in strength of transactivation per se, but could be mimicked, for example, by a 10% decrease in repression.

It is known that the expression of some genes is regulated by the degree of histone acetylation (Struhl, Genes Dev. 12, 599–606, 1998). Use of a relative nontoxic histone deacetylase (HDAC) inhibitor could, conceivably, simplify the interpretation of transcriptional reporter assays. The use of HDAC inhibition to chemically dissect a pathway should unmask some important measures of pathway activation, which could be overlooked in an undissected system. Indeed, it has been previously observed that the presence of trichostatin A (TSA) or butyrate uncovered the inducibility of certain reporters that initially had appeared inactive (Minucci et al., Proc. Natl. Acad. Sci. U.S.A. 94, 11295–300, 1997; Meng et al., Surgery 126, 293–98, 1999).

TSA and butyrate are the most well-studied of the HDAC inhibitors for their effects upon reporters or integrated genes. Various limitations of TSA and butyrate in the applicability to transcriptional assays have been noted in endogenous genes and upon the introduction of exogenous sequences. Butyrate and phenylbutyrate have many functions other than inhibiting HDACs; they have been reported to affect the post-transcriptional modification of other genes (Kitamura et al., Clin. Exp. Immunol. 118, 16–22, 1999) and the depletion of glutamine (Lea & Randolph, Anticancer Res. 18, 2717–22, 1998). There are variable observations that conclude that TSA and other inhibitors do not consistently activate all promoters, and such failures of transcriptional facilitation have included the common general-utility promoters CMV and SV40 (Huang et al., Nature Neurosci. 2, 867–72, 1999; Zhao et al., J. Virol. 73, 5026–33, 1999; Zabel et al., J. Immunol. 163, 2697–703, 1999). Some of the reported transcriptional actions required a specific small recognition element (Li et al., J. Biol. Chem. 274, 7803–15, 1999; Xiao et al., J. Cell. Biochem. 73, 291–302, 1999; Jin & Scotto, Mol. Cell. Biol. 18, 4377–84, 1998), or the activity of a particular co-activator (Sowa et al., Cancer Res. 59, 4266–70, 1999). Furthermore, TSA is not always found to facilitate the detection of positive signal transduction events without interfering with the magnitude of relative transactivation activity (Minucci et al., 1997; Jin et al., 1998). There is, therefore, a need in the art to identify HDAC inhibitors which can be used successfully as general transcription facilitators.

SUMMARY OF THE INVENTION

It is an object of the invention to provide reagents and methods of increasing transcription, which can be used for a variety of purposes.

One embodiment of the invention is a pharmaceutical composition comprising 6-(1,3-Dioxo-1H, 3H-benzo[de]isoquinolin-2-yl)-hexanoic acid hydroxyamide (scriptaid) or a pharmaceutically acceptable salt thereof and a pharmaceutically acceptable carrier.

Another embodiment of the invention is a pharmaceutical composition comprising scriptaid or a pharmaceutically acceptable salt thereof and an expression construct. The expression construct comprises a promoter and a coding sequence for a desired polypeptide. Transcription of the coding sequence is under control of the promoter.

Even another embodiment of the invention is a method of increasing production of a polypeptide. A cell comprising a coding sequence for the polypeptide is contacted with an effective amount of scriptaid or a pharmaceutically acceptable salt thereof. Transcription of the coding sequence is thereby increased relative to transcription in the absence of scriptaid.

Still another embodiment of the invention is a method of increasing production of a polypeptide. A cell-free system comprising a coding sequence for the polypeptide is contacted with an effective amount of scriptaid or a pharmaceutically acceptable salt thereof. Transcription of the coding sequence is thereby increased relative to transcription in the absence of scriptaid.

Yet another embodiment of the invention is a method of increasing production of a therapeutic polypeptide in a diseased cell. The diseased cell is contacted with an effective amount of a composition comprising scriptaid or a pharmaceutically acceptable salt thereof and an expression construct. The expression construct comprises (1) a promoter and (2) a coding sequence for the therapeutic polypeptide. Transcription of the coding sequence is under control of the promoter. Transcription of the coding sequence is thereby increased relative to transcription in the absence of the composition.

Another embodiment of the invention is a kit comprising scriptaid and instructions for a method of increasing production of a polypeptide. The method involves contacting a cell comprising a coding sequence for the polypeptide with an effective amount of scriptaid or a pharmaceutically acceptable salt thereof. Transcription of the coding sequence is thereby increased relative to transcription in the absence of scriptaid.

Even another embodiment of the invention is a method of inhibiting histone deacetylase. The histone deacetylase is contacted with an effective amount of scriptaid or a pharmaceutically acceptable salt thereof. Activity of the histone deacetylase is thereby inhibited relative to activity in the absence of the scriptaid.

Still another embodiment of the invention is a kit comprising scriptaid and instructions for a method of inhibiting histone deacetylase. The method involves contacting the histone deacetylase with an effective amount of scriptaid or a pharmaceutically acceptable salt thereof. Activity of the histone deacetylase is thereby inhibited relative to activity in the absence of the scriptaid.

A further embodiment of the invention is a method of inhibiting histone deacetylase in a neoplastic cell. The neoplastic cell is contacted with an effective amount of scriptaid or a pharmaceutically acceptable salt thereof.

Activity of the histone deacetylase is thereby inhibited relative to activity in the absence of the scriptaid.

Even another embodiment of the invention is a method of treating a patient having a tumor. The tumor is contacted with an effective amount of a composition comprising scriptaid or a pharmaceutically acceptable salt thereof. Activity of histone deacetylase in the tumor is thereby inhibited relative to activity in the absence of the scriptaid.

Yet another embodiment of the invention is a method of monitoring expression of a coding sequence in a cell. A cell comprising the coding sequence is contacted with an effective amount of scriptaid or a pharmaceutically acceptable salt thereof. Expression of the coding sequence is thereby increased relative to expression in the absence of the scriptaid. Expression of the coding sequence is assayed.

The invention thus provides reagents and methods for increasing production of a desired polypeptide, for inhibiting histone deacetylase, and monitoring expression of a polypeptide, as well as therapeutic methods for treating patients with tumors.

BRIEF DESCRIPTION OF THE DRAWINGS

FIG. 2. Structural similarities of TSA, scriptaid, and nullscript.

FIGS. 5A to 5B. Effects of compounds on cell survival. Survival of PANC-1 and MDA-MB-468 in the presence of scriptaid or TSA was determined by trypan-blue exclusion after an 18-hour incubation in the presence of compound. Data represent averages of two to four experiments and SEM. FIG. 5A, scriptaid. FIG. 5B, TSA.

FIG. 6A, p6SBE-luc or p6MBE-luc was cotransfected with pCMV-$\beta$ into PANC-1 cells. Transfected cells were untreated or treated with TGF$\beta$or/and scriptaid for 18 hours. Luciferase activities were proportionally enhanced in the presence of scriptaid. Relative luciferase induction was determined after normalization to the TGF$\beta$-non-inducible pCMV-$\beta$ control, itself subject to scriptaid facilitation (see FIG. 7). Data represent averages of two experiments and SEM. FIG. 6B, total luciferase induction in PANC-1 cells containing the stably integrated p6SBE-luc after treatment with scriptaid or TSA in the absence or presence of TGF$\beta$ (1 ng/ml). FIG. 6C, relative luciferase induction in PANC-1 cells containing the stably integrated p6SBE-luc after treatment with scriptaid or TSA in the absence or presence of TGF$\beta$ (1 ng/ml ) determined after normalization to the values observed with the HDAC inhibitor alone.

FIG. 7A, SV40 promoter and luciferase reporter gene. FIG. 7B, CMV promoter and $\beta$-gal reporter gene. FIG. 7C, human ubiquitin c promoter and $\beta$-gal reporter gene.

DETAILED DESCRIPTION OF THE INVENTION

Figure 1:
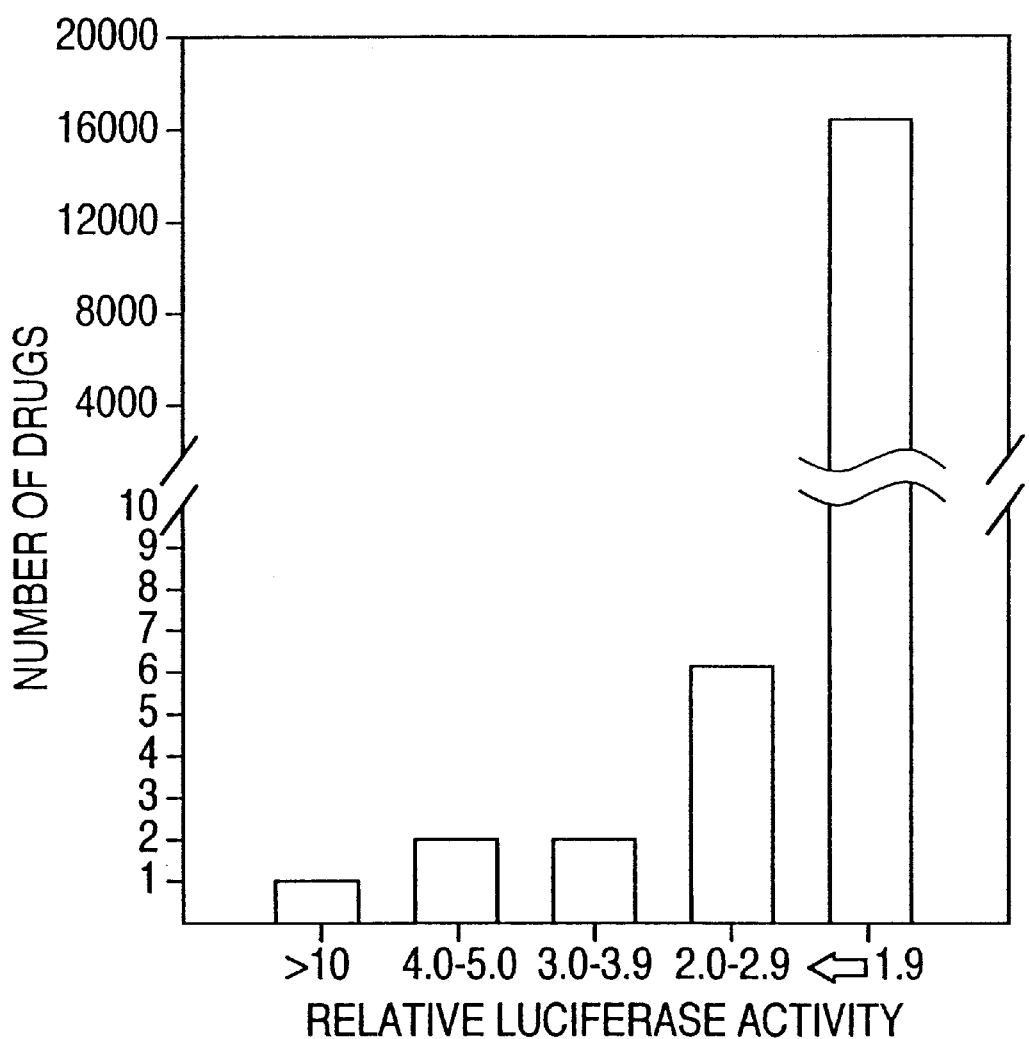
FIG. 1. Distribution of compounds according to their relative luciferase activity, calculated in comparison to untreated cells.

Methods for facilitating transcription generally are discoveries of the present invention, These methods are based on the identification of the compound 6-(1,3-Dioxo-1H,3H-benzo[de]isoquinolin-2-yl)-hexanoic acid hydroxyamide, termed "scriptaid," as a histone deacetylase inhibitor having relatively low toxicity and having the property of robustly and generally facilitating transcription.

Scriptaid

Scriptaid belongs to an existing class of hydroxamic acid-containing HDAC inhibitors. A comparison of the structure of scriptaid and the known HDAC inhibitor TSA is shown in FIG. 2. The structure of 4-(1,3-Dioxo-1H,3H-benzo[de]isoquinolin-2-yl)-N-hydroxy-butyramide, termed "nullscript," also is shown in FIG. 2. Nullscipt, unlike scriptaid, does not facilitate transcription. The hydroxamic acid group and length of the aliphatic linker in scriptaid are believed to be critical for its activity; for example, the aliphatic linkers of TSA and scriptaid are five carbons in length, while the linker in the inactive nullscript is only three carbons long. However, modifications can be made to the aromatic cap of scriptaid without affecting its activity.

Scriptaid possesses a property of general transcriptional facilitation that applies to stably integrated or transiently transfected exogenous constructs, to promoters derived from viruses or an endogenous gene, to multiple reporter genes, and to different cell types and cell lines. Scriptaid does not interfere with the ability of a reporter construct to measure the positive (purely inductive) activation of a transcription factor in response to a known signal transduction stimulus. Scriptaid has advantages over known histone deacetylase inhibitors, such as TSA, with respect to inhibition and transcription facilitation (FIGS. 4 and 7), as well as cellular toxicity (FIGS. 4 and 5), although some degree of cellular toxicity may be a general feature of this class of compounds when used at transcriptionally effective concentrations (Richon et al., 1996).

Scriptaid-containing Compositions

Scriptaid can be provided in a composition for use in various methods of the invention, which are described below. Pharmaceutically acceptable salts of scriptaid may be used so long as they do not adversely affect the activity of scriptaid. Particular salts may be selected and made by those skilled in the art. For example, an alkali metal salt, such as a sodium salt or a potassium salt, an alkaline earth metal salt, such as a calcium salt or a magnesium salt, may be used. Similarly, a salt with an inorganic base, such as an ammonium salt, or a salt with an organic base, such as a triethylamine salt or an ethanolamine salt, may be used.

Scriptaid-containing compositions can comprise a pharmaceutically acceptable carrier, including, but not limited to, saline, buffered saline or other physiologically compatible buffers, dextrose, and water. Preferably, the pharmaceutically acceptable carrier is non-pyrogenic, most preferably it is sterile. If desired, scriptaid-containing compositions can comprise an expression construct encoding one or more desired polypeptides. In the expression construct, transcription of a coding sequence for the desired polypeptide is under the control of a promoter, such as an SV40, CMV, ADH1, T7, or T3 promoter. If the expression construct encodes more than one polypeptide, each polypeptide can be under the control of a separate promoter or one promoter can control transcription of two or more coding sequences.

Many expression constructs suitable for inclusion in scriptaid-containing compositions are commercially available or can be easily constructed using well-known methods, such as recombinant DNA techniques and synthetic techniques.

The polypeptide encoded by the expression construct can be any polypeptide whose transcription is desired in a particular context, including fusion proteins and polypeptides comprising one or more amino acids not found in the naturally occurring version of the polypeptide. For example, the expression construct can encode a reporter polypeptide which comprises a detectable label (e.g., an epitope detectable by a particular antibody or other binding protein) or which produces a detectable product (e.g., β-galactosidase, luciferase, alkaline phosphatase). The desired polypeptide can be a "therapeutic polypeptide," (i.e., a polypeptide with a therapeutic utility), such as peptide or protein hormones (e.g., insulin, growth hormones, calcitonin, parathyroid hormone, adenocorticotropic hormone, thyroid stimulating hormone, prolactin, vasopressin), cytokines (e.g., interferons, such as IFN-α, IFN-β, IFN-γ, and their derivatives; interleukins, such as IL-1, IL-2, IL-3, IL-4, IL-5, IL-6, IL-7, IL-8, IL-9, IL-11, and IL-12), enzymes (e.g., alpha 1 antitrypsin, furin, intestinal enterokinase, PC1/PC3, PC2/PC4), blood coagulation factors (e.g., tissue plasminogen activator, FVIII, FIXa, FXa), and other useful polypeptides (e.g erythropoietin, bone morphogenetic protein, hemoglobin, and tumor suppressor proteins).

Use of Scriptaid to Facilitate Transcription

Because of its ability indiscriminately to facilitate transcriptional activation and detection of a positive transcriptional signal, scriptaid is a useful reagent for transactivation assays in reporter systems, e.g., to monitor expression of particular coding sequences, as well as for use in increasing production of a desired polypeptide for a variety of purposes.

Addition of scriptaid to a transcription system permits the use of difficult-to-transfect cells, the use of less sensitive reporter genes, and the minimization of culture volumes to aid high-throughput compound or biologic screening and for adaptation to robotic handling. A reduction in the signal transduction strength needed to detect the operation of a reporter suggests a utility in the measurement of signal transduction events at a lower and thus more physiologic range. For example, the use of scriptaid would be expected to reduce the requirement for protein overexpression or for high (pharmacologic) levels of ligand often used to facilitate the evaluation of a signaling pathway.

To increase transcription, an intact cell, a cell homogenate, or an in vitro transcription or translation system can be contacted with an effective amount of scriptaid, thereby increasing transcription of one or more coding sequences relative to transcription in the absence of scriptaid. In vitro transcription/translation systems are well known and are described, for example, in Carey et al., *Science* 247, 710–12, 1990; U.S. Pat. No. 6,153,383; and U.S. Pat. No. 5,691,140. Transcription also can be increased in a wide variety of cells, either healthy or diseased, or in homogenates of such cells. An intact cell can be contacted with scriptaid either in vitro or in vivo.

Transcription of an endogenous or exogenous coding sequence can be assayed by detecting mRNA or polypeptide products of the coding sequence. The level of mRNA or polypeptide expression can be determined by methods well known in the art, and either qualitative or quantitative methods can be used. The presence of the polypeptide can be determined, for example, using immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into the polypeptide. mRNA expression can be detected by methods such as Northern blotting and RNase protection assays.

Scriptaid can be used to increase the production of one or more polypeptide s whose expression is desired, including therapeutic and reporter polypeptides. The coding sequence for a desired polypeptide can be present naturally in a cell or in a cell-free system, such as a cell homogenate or in vitro transcription/translation system. Alternatively, the cell or cell-free system can comprise an expression construct that contains the coding sequence. Methods of introducing such expression constructs into cells in vitro and in vivo are well known and include techniques such as include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, and calcium phosphate-mediated transfection.

Polypeptide production can be increased in cells maintained in vitro for commercial or experimental production of the polypeptide. Cell lines useful for polypeptide expression are well known in the art and include *Pichia pastoris* (ATCC ATCC 28485), CHO-K1 (Chinese hamster ovary cell; ATCC CCL61), CHO-K1-derived dihydrofolate reductase (DHFR)-lacking strain, C127I (mouse breast cancer cell; ATCC CRL 1619), BHK (new-born hamster kidney cell; ATCC CCL 10), Vero (African green monkey kidney cell; ATCC CCL-81), COS-1 (ATCC 1650), BHK 21 (ATCC CCL10), C127 (ATCC CRL-1616), HeLa (ATCC CCL2), Jurkat (ATCC TIB-152), Namalwa (ATCC CRL-1432), and Sf-9 (ATCC 1711). Polypeptide production also can be increased in primary cell cultures and explant cultures. If production of a particular polypeptide is to be increased for therapeutic purposes, cells can be removed from a human or non-human patient and contacted with scriptaid or a scriptaid-containing composition. The cells can then be replaced in the same patient or another patient, with or without clonal propagation, as is known in the art. Stem cells, such as bone marrow cells, are particularly useful for this purpose.

Alternatively, diseased cells, such as neoplastic cells from a patient with a tumor or respiratory epithelial cells of a patient with cystic fibrosis, can be contacted with scriptaid in vivo to increase production of a therapeutic polypeptide in the diseased cells. Scriptaid can be provided to these cells by any method suitable for delivery to the particular cell type being treated including, but not limited to, injection, infusion, inhalation, and topical administration. If desired, continuous administration of scriptaid can be provided by a reservoir pump or by an in-dwelling catheter. Other methods of providing scriptaid or a scriptaid-containing composition to a cell, either in vitro or in vivo, include methods such as liposome-mediated fusion, receptor-mediated targeting, and the like, all of which are known and described in the art.

In relation to other members of its class, the optimal concentration of scriptaid (6–8$\mu$M) is similar to those reported for SAHA (2 $\mu$M) and CBHA (4 $\mu$M) (Richon et al., *Proc. Natl. Acad. Sci. U.S.A.* 93, 5705–08, 1996), higher than TSA (1 $\mu$M, as measured in the specific examples, below), and much lower than those reported for HMBA (5000 μM) and EMBA (400 μM) (Richon et al., 1996). Effective amounts of scriptaid, therefore, range from about 1 to 10 μM, preferably 2–8 μM, more preferably 4–8 μM, even more preferably 6–8 μM. The optimal effective amount of scriptaid for a particular application can be determined empirically, using routine screening methods as described, for example, in the specific examples, below.

Methods of Inhibiting Histone Deacetylase

The invention also provides methods of using scriptaid to inhibit histone deacetylase. Histone acetylase can be present in a cell-free system, including a cellular homogenate, or can be present in a cell, such as a neoplastic cell. The histone deacetylase is contacted with an effective amount of scriptaid, thereby inhibiting activity of the histone deacetylase relative to activity in the absence of the scriptaid. Histone acetylase activity preferably is inhibited at least 10, 25, 50, 75, 80, 90, 95, or 100% relative to activity in the absence of scriptaid.

This method can be used therapeutically, for example, in a neoplastic or a tumor cell, to effect differentiation of the cell. Scriptaid or a scriptaid-containing composition can be provided to a cell in vitro, for example, by including it in the culture medium or by adding it directly to medium already present in the culture vessel. If histone acetylase activity in a cell in vivo is to be inhibited, methods of administration such as those described above can be used.

Histone deacetylase inhibition by scriptaid can be used to treat a patient having either a solid or a non-solid (e.g., hematological) tumor. The tumor is contacted with an effective amount of a composition comprising scriptaid. If desired, the composition can comprise a pharmaceutically acceptable carrier, as defined above. Methods of contacting the tumor include, but are not limited to, injection of the composition into a cavity harboring the tumor, direct injection into the tumor, or systemic administration of the composition.

The invention also provides kits that contain scriptaid and instructions for methods of increasing transcription or polypeptide production or for inhibiting histone deacetylase. A kit can contain an expression construct encoding the polypeptide to be expressed. Transfection reagents, such as LipofectAMINE (Life Technologies, Inc.), TransFast™ (Promega), FuGENE™ (Fugent L.L.C.), or DOTAP (Roche) can be included. Nullscript (4-(1,3-Dioxo-1H,3H-benzo[de]isoquinolin-2-yl)-N-hydroxy-butyramide) can be included for use as a control.

All patents and patent applications cited in this disclosure are expressly incorporated by reference herein. The above disclosure generally describes the present invention. A more complete understanding can be obtained by reference to the following specific examples, which are provided for purposes of illustration only and are not intended to limit the scope of the invention.

EXAMPLE 1

Materials and Methods

Reporter Constructs. p6SBE-luc and p6MBE-luc were engineered by inserting six copies of the palindromic SBE (Smad-binding element) or of the MBE (an inactive mutant version) behind the minimal SV40 promoter in the pGL3-promoter vector (Promega, Madison, Wis.) (Dai et al., Cancer Res. 58, 4592–97, 1998).

Cell Lines. PANC-1 and MDA-MB-468 cell lines were purchased from ATCC (Manassas, Va.). Stable transfectants were generated by co-transfection of pcDNA3.1 (Invitrogen, Carlsbad, Calif.) and p6SBE-luc into PANC-1 cells with LipofectAMINE (Life Technologies, Inc.). Transfected cells were diluted and selected in multiple 96-well plates in the presence of 0.5 mg/ml of G418 (Life Technologies, Inc.). Single clones were expanded and tested for basal luciferase expression and TGFβ inducibility. One clone was chosen on basis of high (6 to 8-fold) induction of luciferase by 0.5 ng/ml TGFβ (R&D Systems, Minneapolis, Minn.).

Compound Screening. Each compound of the library (DIVERSet, ChemBridge, San Diego, Calif.) was dissolved and diluted in DMSO at 1 mg/ml. Cells were plated in 96-well cluster plates (Corning, Cambridge, Mass.) and incubated with each compound, after further dilution in culture media to the final concentration of 2 μg/ml, for 16–18 hours. Luciferase activity was measured upon addition of Steady-Glo substrate (Promega). Up to sixteen 96-well plates could be assembled in a Wallac Trilux photodetector (Wallac, Gaithersburg, Md.) for measurement. All readouts from each experiment were compared to the control wells, and a number reflecting the relative increase in luciferase activity was calculated for each chemical using Excel (Microsoft, Redmond, Wash.) spreadsheets.

Immunoblotting Assay of Histone Acetylation. PANC-1 cells were treated with 2 μg/ml of scriptaid (ChemBridge), 0.1 μg/ml, or 0.32 μg/ml of trichostatin A (Sigma, St. Louis, Mo.) for 18 hours in culture media. Treated and untreated cells were harvested with trypsin-EDTA (Life Technologies, Inc.), washed with phosphate-buffered saline (Life Technologies, Inc.), and resuspended in a protein sample buffer. Protein concentration was determined by BCA protein assay reagents (Pierce, Rockford, Ill.). Fifty micrograms of proteins from each sample was loaded on a 12% denaturing polyacrylamide gel. Proteins were subsequently transferred to a nylon membrane (Imobilon P, Millipore, Burlington, Mass.) using Milliblot-Graphite Electroblotter I (Millipore). The nylon membrane was incubated with rabbit anti-human acetyl-lysine antibody (#06-933, Upstate Biotechnology, Waltham, Mass.) at 1:1000 dilution, followed by goat anti-rabbit antibody coupled to horseradish peroxidase (Pierce) at 1:2000 dilution, developed with SuperSignal substrates (Pierce), and detected by film (BioMax, Kodak, Rochester, N.Y.).

Survival Curve. Equal numbers of cells were plated in six-well plates in the absence or presence of scriptaid or TSA at different concentrations. After 18 hours of incubation, cell numbers were determined by trypan-blue exclusion. Percent survival of the treated cells was calculated in comparison to the untreated sample, which was considered to represent 100%.

Transfection Assay. Each transient transfection experiment was done in duplicate in six-well plates. LipofectAMINE (Life Technologies, Inc.) was used as directed by the manufacturer. The DNA-LipofectAMINE mixture was removed from cells after 4–5 hours of transfection, and culture media with or without compounds or TGFβ was then added to the cells. Sixteen to eighteen hours from the start of the transfection, cell lysates were prepared with Reporter Lysis Buffer (Promega) for luciferase and β-gal assays. Luciferase was measured using The Luciferase Assay System (Promega) and β-gal assay was performed as previously described (Dai et al., 1998). Studies of the SV40 promoter included all experiments done with p6SBE-luc, p6MBE-luc, and pGL3-control (Promega) plasmids. Studies of the CMV promoter were done using pCMVβ. (Clonetech, Palo Alto, Calif.), and those of human ubiquitin c promoter were done using pUB6/V5-lacZ (Invitrogen).

EXAMPLE 2

Identification of Scriptaid

Figure 3:
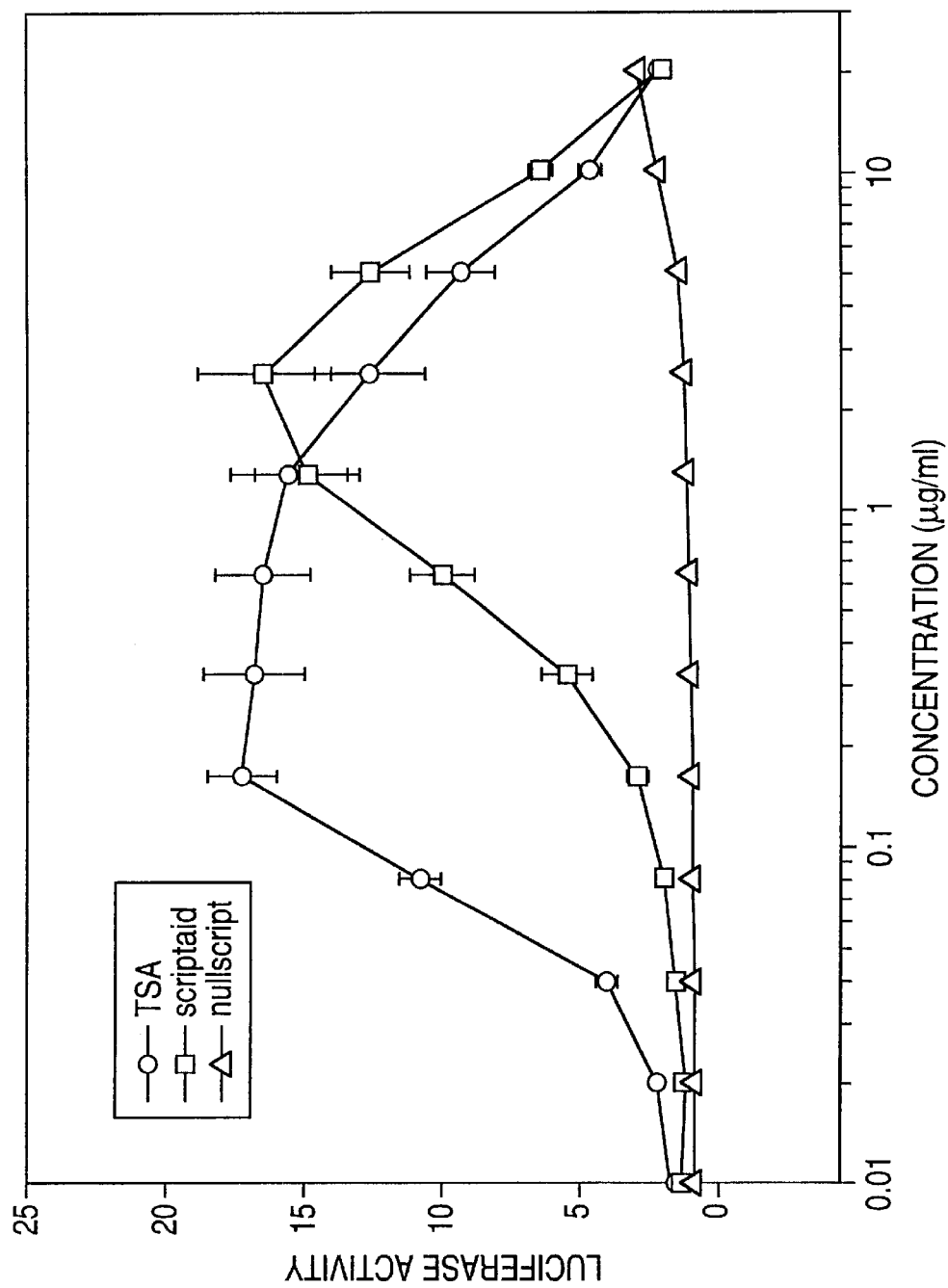
FIG. 3. Dose responses of TSA and scriptaid transcriptional facilitation in a stably transfected cell line. Luciferase activity was determined using PANC-1 cells having stably integrated p6SBE-luc at the indicated concentration of compounds. Data represent averages of two to three experiments and SEM.

The entire library, consisting of 16,320 compounds, was screened. Eleven compounds were associated with a two to five-fold induction of luciferase activity, and one with a twelve-fold activation (FIG. 1). Further studies on the latter compound (ID#217444, 6-(1,3-Dioxo-1H,3H-benzo[de] isoquinolin-2-yl)-hexanoic acid hydroxyamide, we termed scriptaid) are reported here (FIG. 2). A related compound (ID#158497, 4-(1,3-Dioxo-1H,3H-benzo[de]isoquinolin-2-yl)-N-hydroxy-butyramide, we termed nullscript), which did not induce the p6SBE-luc reporter construct in the initial screen, was identified from the library using ChemFinder (Cambridge Soft, Cambridge, Mass.) by its structural similarity to scriptaid (FIG. 2). The results were validated by repeated determinations in the screening assay and subsequently by a dose-response curve performed on PANC-1 cells containing stably integrated p6SBE-luc (FIG. 3).

EXAMPLE 3

Scriptaid as a Novel Inhibitor of Histone Deacetylase

Scriptaid was speculated to be a novel histone deacetylase (HDAC) inhibitor because of its structural similarity to the class of hydroxamic acid-containing HDAC inhibitors, which include trichostatin A (TSA) (FIG. 2). The direct interaction of TSA and a HDAC has been examined by crystallography (Finnin et al., *Science* 401, 188–93, 1999). The hydroxamic acid group of TSA coordinates the zinc atom in the polar pocket of HDAC in the crystal structure of the HDAC-$Zn^{2+}$-TSA complex. The hydroxamic acid group on TSA is attached to a five-carbon (excluding the carbon elements of the hydroxamic acid group or the keto group) aliphatic chain that spans a narrow tube-like pit formed by the surface of HDAC. The double bonds and the methyl-group in the aliphatic chain of TSA (FIG. 2) are not necessary for its inhibitory function (Finnin et al., 1999). The bulky end-group on the opposite end of the aliphatic chain is positioned outside the entrance to the pit. Similar to TSA, scriptaid has a five-carbon linker between a bulky end-group and the hydroxamic acid moiety. Nullscript, which is almost identical to scriptaid except for a three-carbon (rather than five-carbon) linker (FIG. 2), was inactive in transcriptional facilitation at corresponding concentrations (FIG. 3), confirming a minimal requirement for the length of the linker chain expected for this class of HDAC inhibitors.

The use of scriptaid resulted in a greater than 100-fold increase in histone acetylation (FIG. 4) in cultured cells, confirming scriptaid as an HDAC inhibitor.

EXAMPLE 4

Functional Comparison of Scriptaid to Trichostatin A

Figure 4:
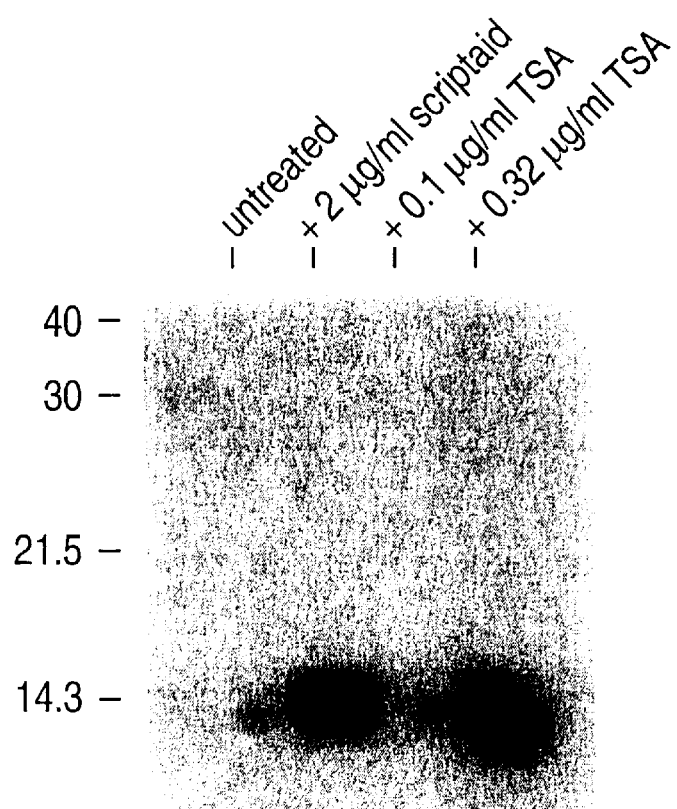
FIG. 4. HDAC inhibition by scriptaid. PANC-1 cells were untreated or treated with scriptaid (2 $\mu$g/ml) or TSA (0.1 or 0.32 $\mu$g/ml). Acetylated histones were detected by anti-human acetyl-lysine antibody immunoblot.

To evaluate the potency of scriptaid, TSA was used as the reference compound in the following experiments. Optimal concentration was determined for both scriptaid and TSA (FIG. 3). Scriptaid worked optimally at 2–2.5 µg/ml (6–8 µM), and TSA activity peaked at 0.32 µg/ml (1 µM). At its optimal concentration for transcriptional facilitation, scriptaid was not lethal to one cell line and had limited effects (80% survival) on another (FIG. 5A). TSA was cytotoxic for two cell lines at its optimal concentration range (FIG. 5B). TSA at its minimal toxic concentration (0.1 µg/ml, 85–90% survival) was less efficient at inhibiting endogenous histone deacetylation (FIG. 4).

Figure 6A:
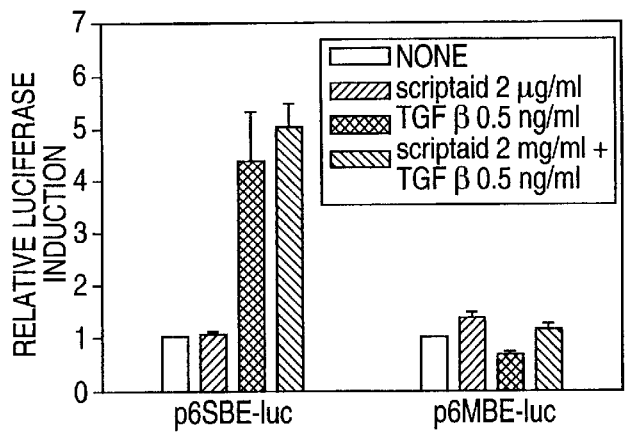
FIGS. 6A–6C. Proportional effects of scriptaid and TSA on the TGF$\beta$/Smad4 signal transduction assay.
Figure 6B:
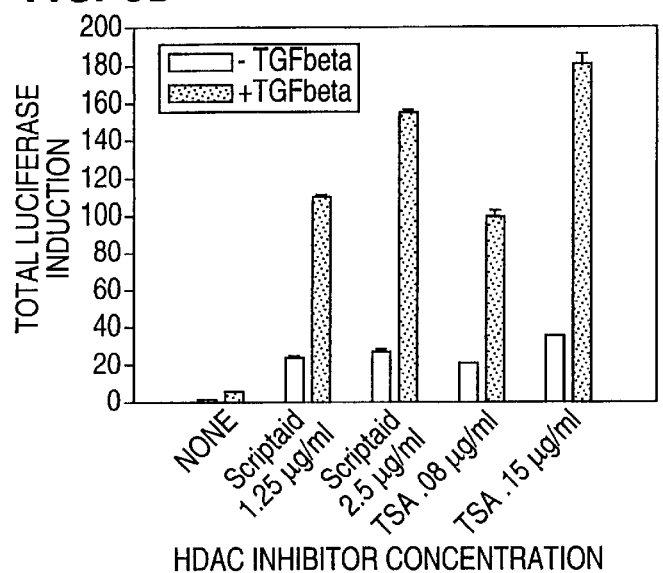
Figure 6C:
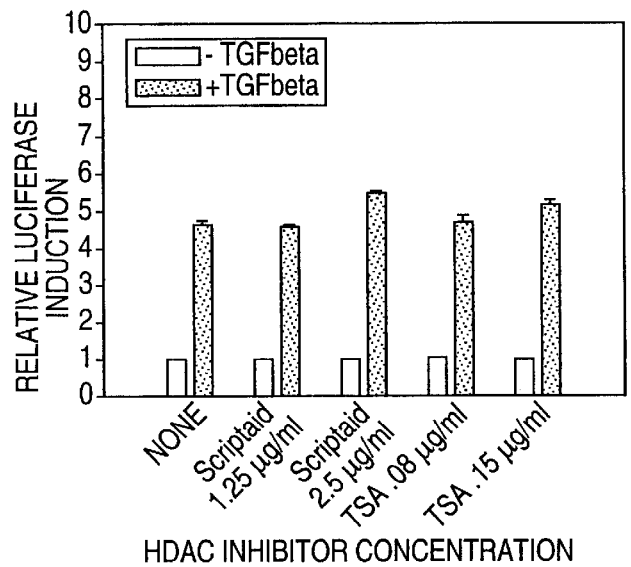

Smad proteins can physically associate with the histone acetylases p300 or CBP, and it has been suggested that the TGFβ/Smad4 signaling pathway might activate gene transcription through such a mechanism (Feng et al., *Genes Dev.* 12, 2153–63, 1998; Janknecht et al., *Genes Dev.* 12, 2114–19, 1998; Pouponnot et al., *J. Biol. Chem.* 273, 22865–68, 1998. It was therefore important to determine whether the manipulation of histone acetylation status would interfere with the results of an assay for relative transcriptional induction mediated by the SBE sequence. It has been shown previously that p6SBE-luc but not p6MBE-luc can be induced by TGFβ treatment (Dai et al., 1998). pCMVβ was therefore co-transfected with p6SBE-luc or p6MBE-luc as a TGFβ-insensitive control. The presence of scriptaid increased the transcription of all three reporters by twelve-fold. Using a normalization for (cotransfected) β-gal expression, the measured magnitude of the ability of TGFβ to induce p6SBE-luc specifically remained the same (FIG. 6A), irrespective of the presence or absence of scriptaid. Scriptaid could thus facilitate transcription independent of a positive inducer of transcription, producing multiplicative rises in reporter activity. Similar effects were seen with either scriptaid or TSA when the reporter construct was stably integrated into the host cell genome (FIGS. 6B and 6C). Scriptaid and TSA can proportionally enhance the induction of an integrated p6SBE-luc construct without interfering with TGFβ-stimulated transcriptional responses.

Figure 7A:
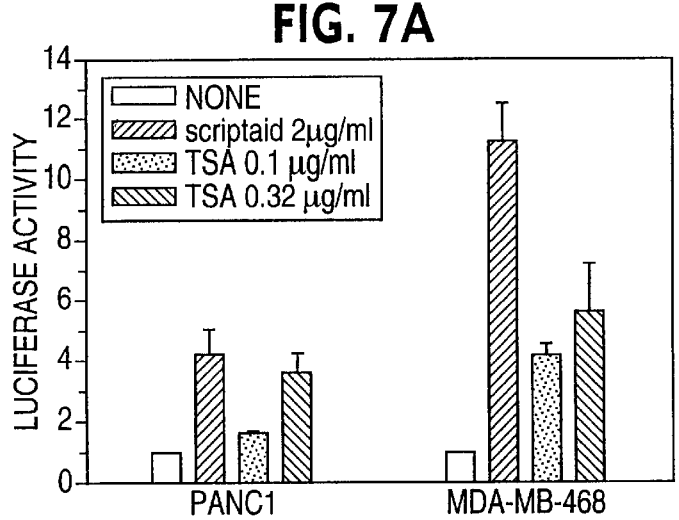
FIGS. 7A–7C. Scriptaid and TSA transcriptional facilitation after transient transfection. PANC-1 or MDA-MB-468 cells were transiently transfected for 4 hours with constructs containing various promoters. Transfected cells were untreated or treated with scriptaid or TSA for 18 hours. Data represent averages of two to five experiments and SEM.
Figure 7B:
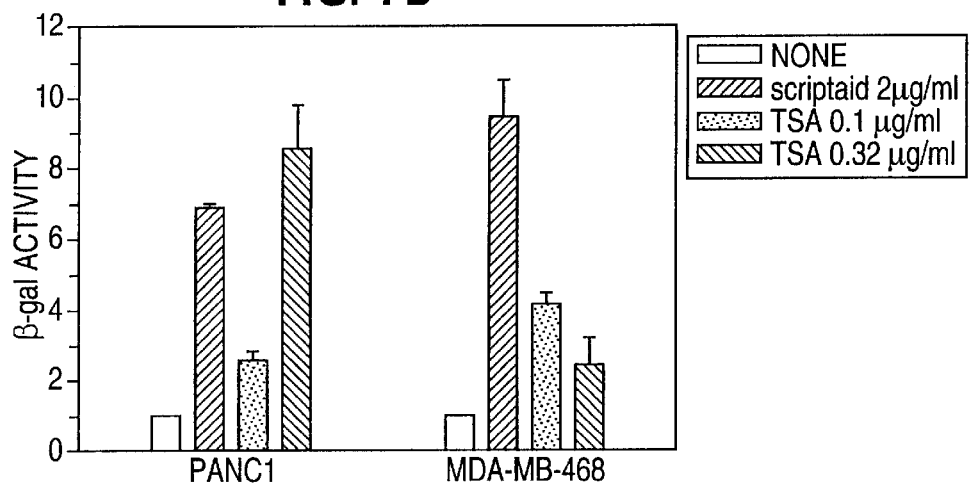
Figure 7C:
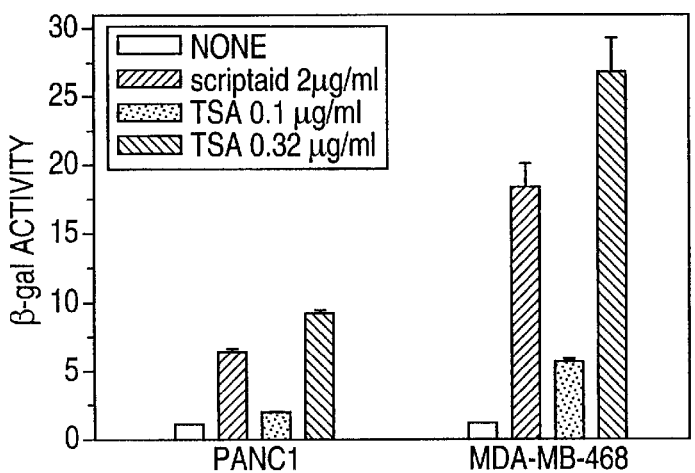

To further evaluate the range of promoter elements subject to scriptaid induction, additional reporters were used in transient transfections. Scriptaid was capable of inducing high expression of p6MBE-luc (FIG. 7A), pCMVβ (FIG. 7B), and pUB6/5-LacZ (FIG. 7C), driven by viral (SV40 and CMV) or human (ubiquitin c, UB6) promoters. This general facilitation of transcription by scriptaid did not depend upon the specificity of the enhancer (SBE vs. MBE), the type of promoter (viral vs. cellular), the product of the reporter gene (luciferase vs. β-gal), nor the integration status of the reporter construct (stable vs. transient). The ability of scriptaid to facilitate transcriptional activation was consistently robust and concentration-dependent in both stable and transient reporter assays (FIGS. 3 and 7). In contrast, the performance of TSA was less predictable at its optimal concentration (FIGS. 7A and 7B, see MDA-MB-468). Lowering the concentration of TSA (0.1 µg/ml) could mitigate this lack of consistency, but in doing so, the efficiency of TSA as an HDAC inhibitor or a general transcription facilitator was significantly compromised (FIGS. 4 and 7).

What is claimed is:
1. A pharmaceutical composition comprising:
   scriptaid or a pharmaceutically acceptable salt thereof; and
   an expression construct comprising:
      a promoter; and
      a coding sequence for a desired polypeptide, wherein transcription of the coding sequence is under control of the promoter.
2. A method of increasing production of a polypeptide, comprising the step of:
   contacting a cell comprising a coding sequence for the polypeptide with an effective amount of scriptaid or a pharmaceutically acceptable salt thereof, whereby transcription of the coding sequence is increased relative to transcription in the absence of scriptaid.
3. The method of claim 2 wherein the cell is a stem cell.
4. The method of claim 2, wherein the cell is a diseased cell.
5. The method of claim 4 wherein the diseased cell is a neoplastic cell.
6. The method of claim 4 wherein the diseased cell is a respiratory epithelial cell.

7. The method of claim 2 wherein the step of contacting is in vitro.

8. The method of claim 7 wherein the cell has been removed from a patient.

9. The method of claim 7 wherein the step of contacting is in vivo.

10. The method of claim 2 wherein the cell comprises an expression construct which contains the coding sequence.

11. The method of claim 2 wherein the polypeptide is a therapeutic polypeptide.

12. The method of claim 2 wherein the polypeptide is a reporter polypeptide which produces a detectable product.

13. The method of claim 2 wherein the polypeptide is a reporter polypeptide which comprises a detectable label.

14. The method of claim 9 wherein the scriptaid is provided by injection.

15. The method of claim 9 wherein the scriptaid is provided by infusion.

16. The method of claim 9 wherein the scriptaid is provided by inhalation.

17. The method of claim 9 wherein the scriptaid is provided by topical administration.

18. The method of claim 9 wherein the scriptaid is provided by a reservoir pump.

19. The method of claim 9 wherein the scriptaid is provided by a catheter.

20. A method of increasing production of a polypeptide, comprising the step of:

contacting a cell-free system comprising a coding sequence for the polypeptide with an effective amount of scriptaid or a pharmaceutically acceptable salt thereof, whereby transcription of the coding sequence is increased relative to transcription in the absence of scriptaid.

21. The method of claim 20 wherein the polypeptide is a therapeutic polypeptide.

22. The method of claim 20 wherein the polypeptide is a reporter polypeptide which produces a detectable product.

23. The method of claim 20 wherein the polypeptide is a reporter polypeptide which comprises a detectable label.

24. A method of increasing production of a therapeutic polypeptide in a diseased cell, comprising the step of:

contacting the diseased cell with an effective amount of a composition comprising:
scriptaid or a pharmaceutically acceptable salt thereof; and
an expression construct comprising (1) a promoter and (2) a coding sequence for the therapeutic polypeptide, wherein transcription of the coding sequence is under control of the promoter, whereby transcription of the coding sequence is increased relative to transcription in the absence of the scriptaid.

25. A kit comprising:

scriptaid or a pharmaceutically acceable salt thereof; and instructions for the method of claim 2.

26. The kit of claim 25 further comprising an expression construct comprising:

a promoter; and a coding sequence for a desired polypeptide, wherein transcription of the coding sequence is under control of the promoter.

27. The kit of claim 26 wherein the desired polypeptide is a therapeutic polypeptide.

28. The kit of claim 26 wherein the polypeptide is a reporter polypeptide which produces a detectable product.

29. The kit of claim 26 wherein the polypeptide is a reporter polypeptide which comprises a detectable label.

30. The kit of claim 25 further comprising a transfection reagent.

31. The kit of claim 25 further comprising 4-(1,3-Dioxo-1H,3Hbenzo[de]isoquinolin-2-yl)-N-hydroxy-butyramide (nullscript).

* * * * *

UNITED STATES PATENT AND TRADEMARK OFFICE
CERTIFICATE OF CORRECTION

PATENT NO.    : 6,544,957 B2
DATED         : April 8, 2003
INVENTOR(S)   : Scott E. Kern et al.

It is certified that error appears in the above-identified patent and that said Letters Patent is hereby corrected as shown below:

<u>Column 11,</u>
Line 5, "7" has been replaced by -- 2 --.

Signed and Sealed this

Sixteenth Day of September, 2003

JAMES E. ROGAN
*Director of the United States Patent and Trademark Office*